(12) United States Patent
Itsuji (10) Patent No.: US 8,536,530 B2
(45) Date of Patent: Sep. 17, 2013

(54) TERAHERTZ WAVE TRANSCEIVER AND TOMOGRAPHIC IMAGE ACQUISITION APPARATUS

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 232 days.

(21) Appl. No.: 13/190,875

(22) Filed: Jul. 26, 2011

(65) Prior Publication Data

US 2012/0032083 A1    Feb. 9, 2012

(30) Foreign Application Priority Data

Aug. 5, 2010 (JP) ................................. 2010-175825

(51) Int. Cl.
*G01J 5/02*  (2006.01)
(52) U.S. Cl.
USPC ...................................................... 250/341.1
(58) Field of Classification Search
USPC ...................................................... 250/341.1
See application file for complete search history.

(56) References Cited

U.S. PATENT DOCUMENTS

2001/0038074 A1* 11/2001 Zhang et al. ............... 250/341.8

FOREIGN PATENT DOCUMENTS

WO            01/77646 A1    10/2001

* cited by examiner

*Primary Examiner* — David Porta
*Assistant Examiner* — Hugh H Maupin
(74) *Attorney, Agent, or Firm* — Canon U.S.A. Inc., IP Division (57) ABSTRACT

A terahertz wave transceiver configured to generate and detect terahertz waves based on time-domain spectroscopy includes a photoconductive device having a photoconductive film, a first electrode, and a second electrode. An excitation light illumination region is formed between the first and second electrodes. A bias applying unit applies a bias between the first electrode and the second electrode to generate the terahertz wave in the excitation light illumination region. A current detection unit detects a terahertz-wave current that is a component of a current generated in the excitation light illumination region and that is generated by an electric field of a received terahertz wave arriving from the outside. A current drawing unit draws a current originating from the bias applied by the bias applying unit. An adjustment unit determines the amount of the current drawn, based on the amount of the bias applied by the bias applying unit.

7 Claims, 5 Drawing Sheets

TERAHERTZ WAVE TRANSCEIVER AND TOMOGRAPHIC IMAGE ACQUISITION APPARATUS

BACKGROUND OF THE INVENTION

1. Field of the Invention

The present invention relates to an apparatus configured to generate and detect a terahertz wave to measure a time-domain waveform of the terahertz wave and a tomographic image acquisition apparatus using such an apparatus. More particularly, the present invention relates to an apparatus configured to generate and detect a terahertz wave using a single device (hereinafter such an apparatus will be referred to as a transceiver) and a tomographic image acquisition apparatus using such a transceiver.

2. Description of the Related Art

A terahertz (THz) wave is an electromagnetic wave with a frequency in an arbitrary frequency band within a range from 0.03 THz to 30 THz. This frequency range includes frequencies or bands of frequency at which characteristic absorption occurs due to structures or states of substances such as biological molecules. This characteristic absorption feature is useful to nondestructively analyze or identify a substance, and thus associated techniques have been developed. One example of an expected application is a safety imaging technique that can enhance or potentially replace an X-ray imaging technique. Another example of an application of terahertz waves is the development of a high-speed communication technique.

When a terahertz wave used is in the form of a pulse, it is known to sample the terahertz wave using excitation light in the form of an ultra-short light pulse thereby measuring the terahertz wave reaching a detector. This technique is called THz-TDS (THz-Time Domain Spectroscopy). In many THz-TDS apparatuses, a photoconductive device is used as a generating device or a detecting device because of its high efficiency in generation and detection of terahertz waves. The photoconductive device may be produced using a semiconductor film (also referred to as a photoconductive film in the present description) on which electrodes including an antenna are formed. More specifically, the electrodes are disposed so as to oppose each other via a gap (also referred to as an excitation light illumination region in the present description). The excitation light illumination region is illuminated with an ultra-short light pulse to instantaneously make the gap between the two electrodes conductive thereby generating or measuring a terahertz wave by using the sampling technique. WO2001/077646A1 discloses a terahertz wave transceiver, which is an example of a THz-TDS apparatus, configured to generate and detect a terahertz wave using a single photoconductive device. In this terahertz wave transceiver disclosed in WO2001/077646A1, excitation light is split into to two beams of light, i.e., pump light and probe light and a terahertz wave is generated by the pump light. The intensity of the generated terahertz wave is modulated using a chopper, and a current signal generated by probe light illuminating the gap portion and the electric field of the terahertz wave is detected using a lock-in detection method.

In the configuration of the apparatus disclosed in WO2001/077646A1, the current signal is detected from the excitation light illumination region while applying a voltage to the excitation light illumination region of the photoconductive device thereby generating the terahertz wave. Therefore, the current detection unit, which detects the current generated in the excitation light illumination region, receives a current I generated by the voltage used to generate the terahertz wave in addition to the terahertz-wave current δi generated by the electric field of the terahertz wave. For example, in a case where low-temperature grown gallium arsenide (LT-GaAs) is used as the photoconductive film of the photoconductive device, the terahertz-wave current δi is as small as a few nA to a few ten nA, but the current I is a few μA to a few ten μA, which is greater than the terahertz-wave current δi. To detect these currents, the current detection unit may be configured to have a high sensitivity as possible within a range in which no saturation occurs in the output of the current detection unit. However, in the technique disclosed in WO2001/077646A1, the large value of the current I relative to the terahertz-wave current δi makes it difficult to detect the terahertz-wave current δi with high sensitivity.

SUMMARY OF THE INVENTION

According to one aspect of the present invention, there is provided a terahertz wave transceiver configured to generate and detect terahertz waves based on time-domain spectroscopy, including a photoconductive device including a photoconductive film, a first electrode, and a second electrode configured such that the first and second electrodes are disposed on the photoconductive film and such that the first and second electrodes oppose each other via an excitation light illumination region, a bias applying unit connected to the first electrode and configured to apply a bias between the first electrode and the second electrode to generate a terahertz wave in the excitation light illumination region, a current detection unit connected to the second electrode and configured to detect a terahertz-wave current that is a component of a current generated in the excitation light illumination region and that is generated by an electric field of a received terahertz wave, and a current drawing unit connected to the second electrode and configured to draw a current originating from the bias applied by the bias applying unit, wherein the current drawing unit includes an adjustment unit configured to determine the amount of the current drawn, based on the amount of the bias applied by the bias applying unit.

According to another aspect of the present invention, the current drawing unit draws the current generated in the photoconductive device due to the bias so as to prevent or reduce flowing of the bias current into the current detection unit. This makes it possible for the current detection unit to detect the terahertz-wave current caused by the electric field of the terahertz wave without being influenced by the bias current, and thus it becomes possible to detect the terahertz-wave current with high sensitivity.

Further aspects of the present invention will become apparent from the following description of exemplary embodiments with reference to the attached drawings.

DESCRIPTION OF THE EMBODIMENTS

The present invention provides a technique to draw a current generated in a photoconductive device due to a bias so as to prevent or reduce flowing of this bias current into a current detection unit. The amount of the current drawn is determined based on the amount of the bias applied. Based on this idea, the invention provides a terahertz wave transceiver and a tomographic image acquisition apparatus using a terahertz wave transceiver having a configuration basically similar to that described above in the SUMMARY OF THE INVENTION section.

Next, specific embodiments of the invention are described below with reference to the accompanying drawings.

First Embodiment (Terahertz Wave Transceiver)

Figure 1:
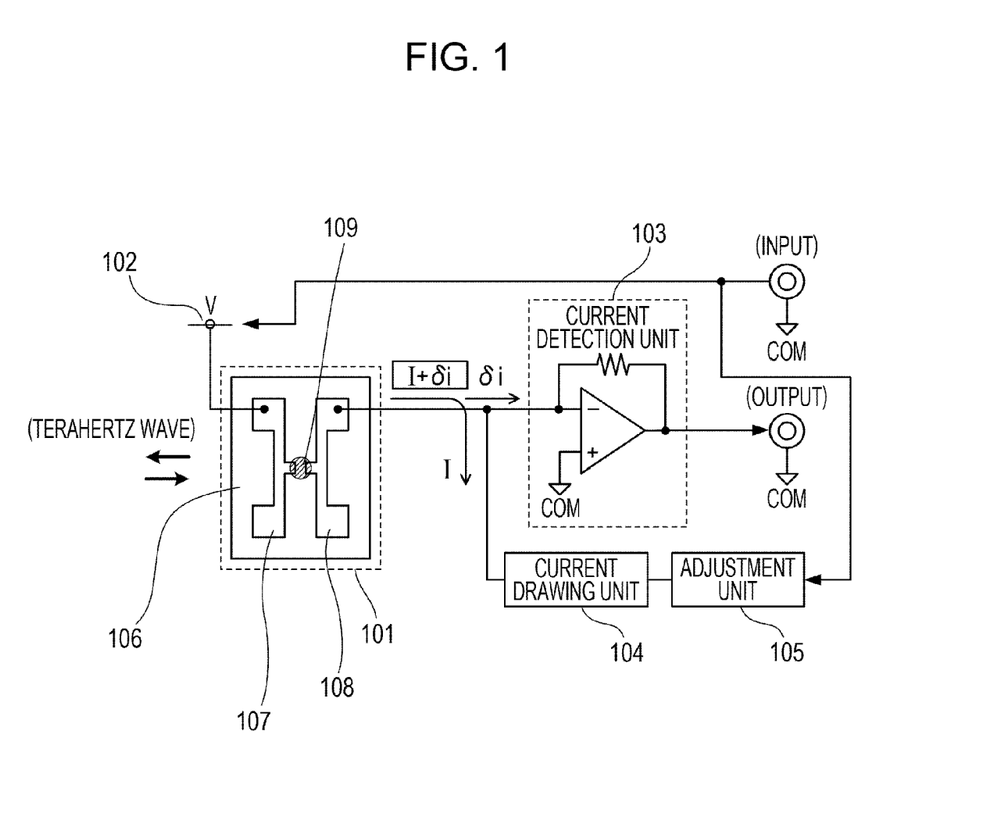
FIG. 1 is a schematic diagram illustrating an example of a configuration of a terahertz wave transceiver according to an embodiment of the present invention.

FIG. 1 illustrates a terahertz wave transceiver according to a first embodiment of the present invention. As shown in FIG. 1, the terahertz wave transceiver includes a photoconductive device 101, a bias applying unit 102, a current detection unit 103, a current drawing unit 104, and an adjustment unit 105. The photoconductive device 101 is a unit that generates a terahertz wave. The photoconductive device 101 is configured based on a configuration widely employed in THz-TDS apparatuses. More specifically, the photoconductive device 101 includes a photoconductive film 106, a first electrode 107, and a second electrode 108. In FIG. 1, an excitation light illumination region 109 denotes a region that is illuminated with excitation light. The first electrode 107 and the second electrode 108 are disposed on the photoconductive film 106 such that they oppose each other via the excitation light illumination region 109. As shown in FIG. 1, the first electrode 107 and the second electrode 108 each have a projecting part formed such that the excitation light illumination region 109 is located between the projecting parts. Typically, the projecting parts are disposed such that they oppose each other via a gap of a few μm. These projecting parts chiefly function as an antenna for a terahertz wave. Note that FIG. 1 illustrates an upper surface of the photoconductive device 101. The excitation light strikes the excitation light illumination region 109 from a direction normal to the page of FIG. 1. In this situation, a terahertz wave propagates in the direction normal to the page.

The excitation light illumination region 109 is illuminated with pump light and probe light as excitation light based on the THz-TDS technique. The pump light is used to generate the terahertz wave, and the probe light is used to detect the terahertz wave. Typically, femto-second laser light may be used as the excitation light, and the repetition frequency may be set to 10 MHz. The size of the excitation light illumination region 109 may be set within a range of a few μm to a few ten μm, depending on the wavelength of the excitation light used. In an alternative embodiment, the projecting parts of the first electrode 107 and the second electrode 108 may overlap the excitation light illumination region 109. The photoconductive film 106 generates carriers in response to excitation light irradiating the photoconductive film 106. The photoconductive film 106 is formed of a thin semiconductor film. The type of the thin semiconductor film is selected according to the wavelength of the excitation light. For example, in a case where the wavelength of the excitation light is 0.8 μm, low-temperature grown gallium arsenide (LT-GaAs) may be used as the thin semiconductor film. When the wavelength of the excitation light is 1.55 μm, low-temperature grown indium gallium arsenide (LT-InGaAs) may be used. Note that materials are not limited to those described above.

The first electrode 107 and the second electrode 108 are elements by which to apply a bias voltage to the excitation light illumination region 109. A current produced by carriers generated in the excitation light illumination region 109 is output to the current detection unit 103 (which will be described in detail later) via the first electrode 107 and the second electrode 108. Materials for the first electrode 107 and the second electrode 108 may be selected so that ohmic contacts to the photoconductive film 106 used are achieved. The bias applying unit 102 serves to apply a bias to a part, in the excitation light illumination region 109, where projecting parts of the first electrode 107 and the second electrode 108 oppose each other. The bias applying unit 102 is connected to the first electrode 107. On the other hand, the second electrode 108 is connected to the current detection unit 103 described below and is virtually grounded with respect to a reference potential (denoted by COM in FIG. 1) of the bias applying unit 102. The bias voltage applied by the bias applying unit 102 is used to generate the terahertz wave. More specifically, illumination of the pump light causes carriers to be generated in the excitation light illumination region 109, and the generated carriers are accelerated by the applied bias voltage whereby the terahertz wave is radiated.

The carriers accelerated by the bias voltage are sent as a current to the current detection unit 103 connected to the second electrode 108. In the present description, this current is referred to as a bias current I. Typically, the applied bias voltage may be set within the range of a few volts to a few hundred volts. The specific value of the bias voltage applied by the bias applying unit 102 is determined with reference to a signal input via a terminal INPUT shown in FIG. 1. The bias voltage applied by the bias applying unit 102 may be in the form of a DC voltage or a DC voltage. In particular, when an AC signal including an AC component is used, it is possible to modulate the intensity of the generated terahertz wave. The value of the bias current I depends on the applied bias voltage, the intensity of the pump light, and the material of the photoconductive film 106. In the case where the photoconductive film 106 is made of LT-GaAs, the bias current I is in a range from a few μA to a few ten μA. In the case where the photoconductive film 106 is made of LT-InGaAs, the bias current I is a few ten to a few hundred times greater.

The photoconductive device 101 outputs a current including the bias current I and a current caused by an electric field of the terahertz wave striking the photoconductive device 101. In the present description, the latter current component is referred to as a terahertz-wave current δi. The terahertz-wave current δi is generated in such a manner that illumination of the probe light generates carriers in the excitation light illumination region 109, the generated carriers are moved by the electric field of the terahertz wave, and, as a result, the terahertz-wave current δi is generated. In practice, because the applied bias voltage is given by the bias applying unit 102, it can be said that the current corresponding to the change in the applied voltage caused by the electric field of the terahertz wave is output as the terahertz-wave current δi. The value of the terahertz-wave current δi depends on the electric field of the terahertz wave striking the photoconductive device 101, the intensity of the probe light, and the material of the photoconductive film 106. In the case where the photoconductive film 106 is made of LT-GaAs, the terahertz-wave current δi is in a range of a few nA to a few ten nA. In the case where the photoconductive film 106 is made of LT-InGaAs, the terahertz-wave current δi is in a similar range. As described above, the terahertz-wave current δi can be smaller 3 orders of magnitude smaller than bias current I.

The current detection unit 103 is a circuit that converts a current signal generated by the photoconductive device 101 into a voltage signal with a measurable level. The current detection unit 103 is connected to the second electrode 108 of the photoconductive device 101. In the current detection unit 103, inputs thereof are virtually grounded by an electric circuit with respect to the reference potential COM of the transceiver. In the present description, the conversion ratio of the current signal to the voltage signal is referred to as a current-to-voltage conversion ratio. The current-to-voltage conversion ratio is selected within a range that allows the current detection unit 103 to provide an output corresponding to the current signal input to the current detection unit 103 without causing the output of the current detection unit 103 to exceed a rated value specified for the circuit and without causing saturation. To increase the signal-to-noise ratio of the apparatus using the transceiver, the current-to-voltage conversion ratio may be set to be as large as possible. The current detection unit 103 may include a lock-in detection system. More specifically, the lock-in detection system is disposed at a final stage of a circuit that performs the current-to-voltage conversion. In the case where the current detection unit 104 includes the lock-in detection system, the circuit that performs the current-to-voltage conversion is set such that the amplitude of the signal output therefrom does not exceed the input rating of the lock-in detection system.

Figure 5A:
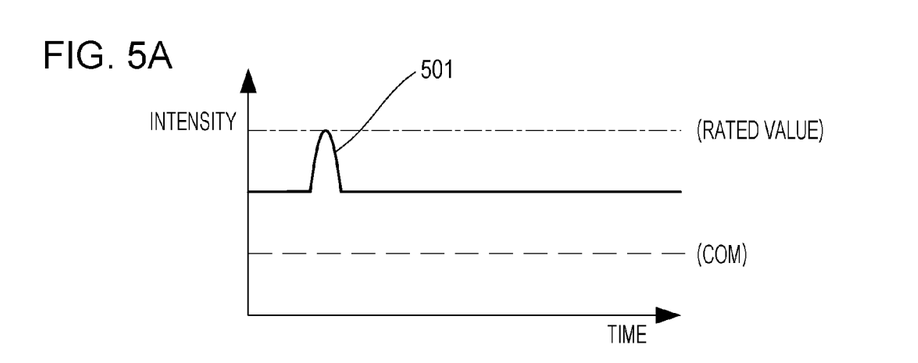
FIGS. 5A to 5C are diagrams illustrating an operation of a terahertz wave transceiver.
Figure 5B:
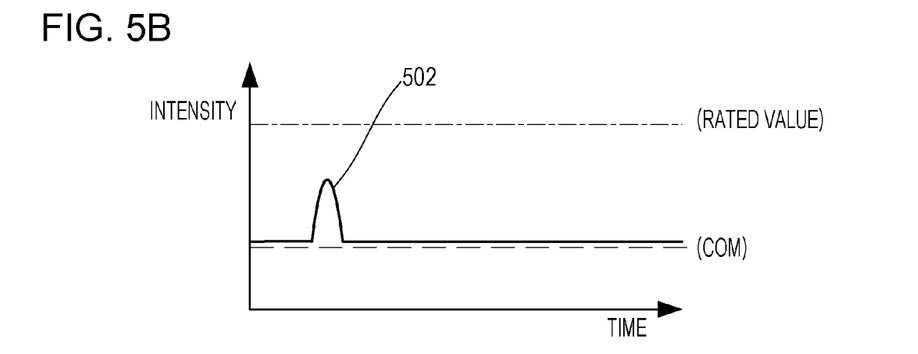
Figure 5C:
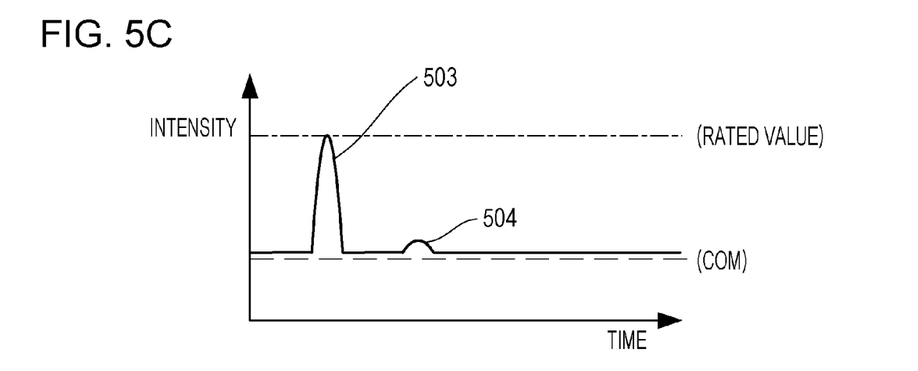

Referring to FIGS. 5A to 5C, a concept of an operation of the terahertz wave transceiver according to the present embodiment is described below. FIGS. 5A to 5C illustrate outputs of the current detection unit 103. In these figures, each horizontal axis illustrates a difference in time between the pump light and the probe light wherein the time advances with increasing time difference. In FIGS. 5A to 5C, for simplicity of explanation, no modulation is performed on the intensity of the terahertz wave. As described above, the current output from the photoconductive device 101 includes the bias current I and the terahertz-wave current δi where the bias current I is greater than the terahertz-wave current δi. In a case where the current output from the photoconductive device 101 is directly detected by the current detection unit 103, it is necessary to set parameters such that the output of the current detection unit 103 does not exceed the rating. In FIG. 5A, a base line of the terahertz wave 501 is located between the rating and the reference potential COM of the transceiver. This occurs because the bias current I is steadily input to the current detection unit 103. An offset of the base line from the reference potential COM can be a factor that limits the current-to-voltage conversion ratio of the current detection unit 103. In the present embodiment of the invention, the influence of the bias current δi is suppressed and the base line of the terahertz wave 502 is set to be close to the reference potential COM of the transceiver (FIG. 5B). As a result, the terahertz-wave current δi becomes a major signal 503 in the detection performed by the current detection unit 103. Therefore, the current detection unit 103 can be set to have a higher current-to-voltage conversion ratio for the terahertz-wave current δi. This makes it possible to detect the terahertz-wave current δi with higher sensitivity. Thus, it becomes possible to detect even a weak signal 504 that would otherwise be hidden behind noise (FIG. 5C).

Referring again to FIG. 1, to suppress the influence of the bias current I, the transceiver according to the present embodiment of the invention has the current drawing unit 104 and the adjustment unit 105. The current drawing unit 104 is connected to a node between the second electrode 108 of the photoconductive device 101 and the input of the current detection unit 103. The current drawing unit 104 serves to draw the bias current I from the total current output from the photoconductive device 101 such that only the terahertz-wave current δi is input to the current detection unit 103. The adjustment unit 105 adjusts the amount of the current drawn by the current drawing unit 104 to minimize the influence the bias current I.

Figure 4A:
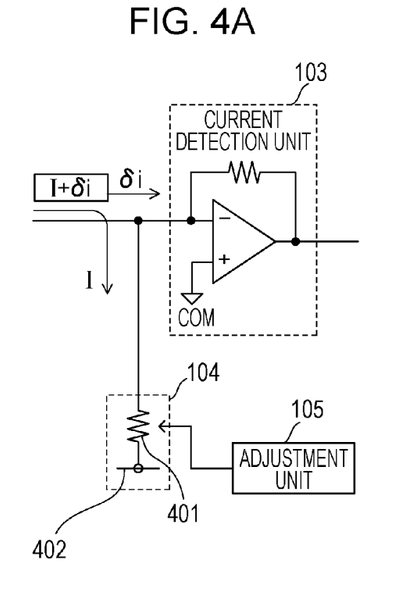
FIGS. 4A to 4C are diagrams illustrating an example of a configuration associated with a current drawing unit.
Figure 4B:
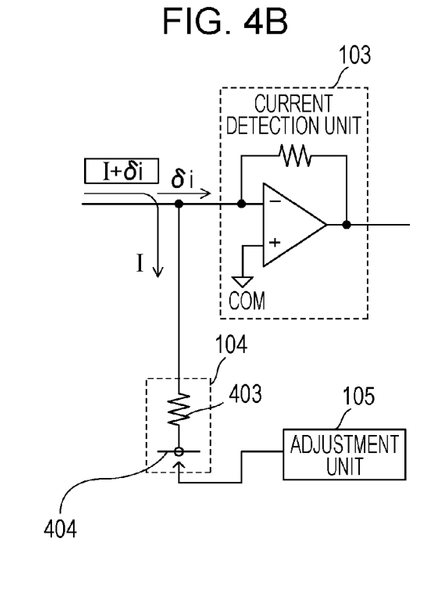
Figure 4C:
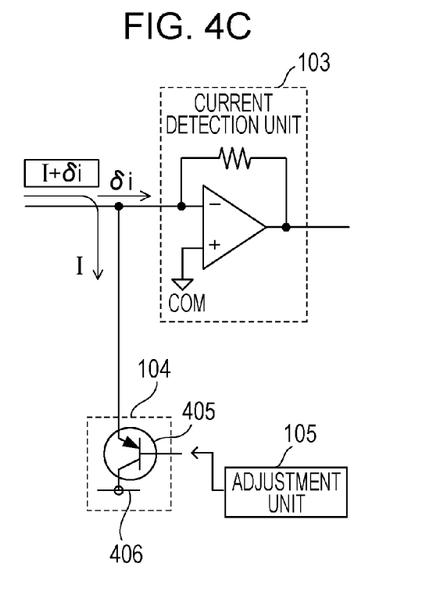

FIGS. 4A to 4C illustrates examples of configurations of the current drawing unit 104. In the example shown in FIG. 4A, the current drawing unit 104 is configured using a variable resistance unit 401 and a drawing bias applying unit 402. The drawing bias applying unit 402 provides a bias voltage determined with respect to the reference potential COM serving as a virtual ground for the current detection unit 103. Therefore, the bias voltage given by the drawing bias applying unit 402 is mainly applied to the variable resistance unit 401. The adjustment unit 105 adjusts the amount of the drawn current by adjusting the resistance of the variable resistance unit 401. In the example shown in FIG. 4B, the current drawing unit 104 is configured using a resistor 403 and a drawing bias adjustment unit 404. The drawing bias adjustment unit 404 provides a bias voltage determined with respect to the reference potential COM serving as a virtual ground for the current detection unit 103. Therefore, the bias voltage given by the drawing bias adjustment unit 404 is mainly applied to the resistor 403. The adjustment unit 105 adjusts the amount of the drawn current by adjusting the amount of the bias applied by the drawing bias adjustment unit 404. In the example shown in FIG. 4C, the current drawing unit 104 is configured using a current sink circuit 405 and a drawing bias applying unit 406. The specific value of the bias voltage applied by the drawing bias applying unit 406 is determined with reference to the reference potential COM serving as the virtual ground for the current detection unit 103. The current sink circuit 405 is realized using a semiconductor device such as a transistor. The bias voltage given by the drawing bias applying unit 406 is mainly applied to the current sink circuit 405. The adjustment unit 105 adjusts the magnitude of the drawn current by changing the bias condition (such as a bias voltage or a bias current) of the semiconductor device. Note that the configuration of the current drawing unit 104 is not limited to those described above, but many other configurations may be employed as long as a current corresponding to the bias current I can be drawn.

As described above, the adjustment unit 105 is connected to the current drawing unit 104. The amount of the bias applied by the bias applying unit 102 is, as described above, adjusted in accordance with an external signal input via INPUT. More specifically, the adjustment unit 105 refers to the external signal for the bias adjustment, and determines the amount of the bias drawn by the current drawing unit 104 according to the external signal. For this purpose, the adjustment unit 105 is connected to a signal line via which the external signal is received. In the transceiver according to the present embodiment of the invention, the amount of the bias applied by the bias applying unit 102 and the amount of the current defined by the current drawing unit 104 are defined as a function of the external signal input via INPUT. More specifically, the relationship between the amount of the applied bias and the amount of the bias current corresponding thereto is defined in advance for each photoconductive device 101 used and the information indicating this relationship is stored in the adjustment unit 105 so that the amount of the current drawn by the current drawing unit 104 changes with substantially no delay in response to the change in the bias applied by the bias applying unit 102. That is, when a particular amount of applied bias is given, the corresponding bias current I is predicted and adjusted. Thus, this adjustment method may be called a feed forward adjustment method. This method allows only the terahertz-wave current δi to be input to the current detection unit 103 and thus the current detection unit 103 can be set to have a high current-to-voltage conversion ratio, which makes it possible to achieve high sensitivity in the detection. Furthermore, it is possible to electrically modulate the intensity of the terahertz wave, which allows it to acquire a signal at a higher speed than is possible by a mechanical method.

In the present embodiment, as described above, the terahertz wave transceiver includes the single photoconductive device and the bias applying unit wherein the photoconductive device includes the first electrode and the second electrode formed on the photoconductive film such that the first electrode and the second electrode oppose each other via the excitation light illumination region, and the bias applying unit is configured to apply the bias voltage to the excitation light illumination region to generate the terahertz wave. The terahertz wave transceiver also includes the current detection unit and the current drawing unit wherein the current detection unit is configured to detect the terahertz-wave current generated by the electric field of the terahertz wave coming from the outside, and the current drawing unit is configured to drawn the current caused by the bias voltage applied by the bias applying unit. The current drawing unit includes the adjustment unit to determine the amount of the drawn current based on the amount of the bias voltage applied by the bias applying unit. That is, in the terahertz wave transceiver according to the present embodiment, the current drawing unit 104 draws the bias current I generated by the photoconductive device 101 so that the bias current I is prevented from being input to the current detection unit 103 or inputting of the bias current I to the current detection unit 103 is suppressed. As a result, the advantages described above are achieved. In particular, in a case where a bias voltage including an AC component is applied by the bias applying unit 102 to the photoconductive device 101, the terahertz wave transceiver according to the present embodiment refers to the amount of this bias voltage and determines the amount of the bias current I drawn by the current drawing unit 104 based on the amount of this bias voltage. This makes it possible to prevent or reduce flowing of the bias current I into the current detection unit 103 even when a change occurs in the bias voltage. Therefore it becomes possible to electrically modulate the intensity of the generated terahertz wave, and it becomes easy to increase the speed of acquiring the time-domain waveform of the terahertz wave compared to the mechanical modulation.

Second Embodiment (Tomographic Image Acquisition Apparatus)

Figure 2A:
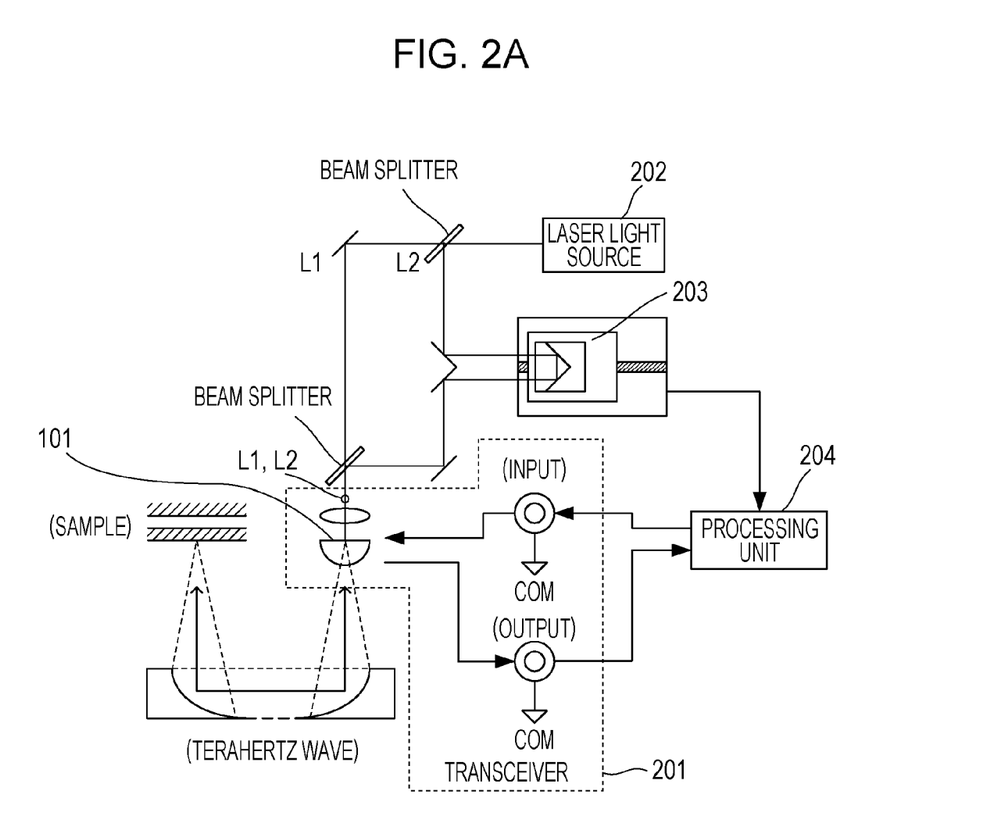
FIG. 2A is a diagram illustrating an example of a configuration of a tomographic image acquisition apparatus according to an embodiment of the present invention.

A second embodiment is described below. In this second embodiment, the terahertz wave transceiver according to the first embodiment described above is used, by way of example, in a tomographic image acquisition apparatus. FIG. 2A schematically illustrates a configuration of the tomographic image acquisition apparatus according to the present embodiment. The tomographic image acquisition apparatus according to the present embodiment includes a laser light source 202, an optical delay unit 203, and a processing unit 204, in addition to the terahertz wave transceiver 201 according to the first embodiment described above.

Note that parts shown in FIG. 1 are not shown in FIG. 2A for simplicity. That is, the bias applying unit 102, the current detection unit 103, the current drawing unit 104, and the adjustment unit 105 are not shown, but FIG. 2A illustrates a simplified configuration in which terminals INPUT and OUTPUT are connected to the photoconductive device 101. The terminal INPUT serves as a terminal for inputting a signal according to which to adjust the bias voltage applied by the bias applying unit 102 to the photoconductive device 101. The adjustment unit 105 refers to this signal and determines the amount of the current drawn by the current drawing unit 104 based on the signal. The terminal OUTPUT serves as a terminal for outputting an output signal of the current detection unit 103. In many cases, the signal output via the terminal OUTPUT is in the form of a voltage signal.

Figure 2B:
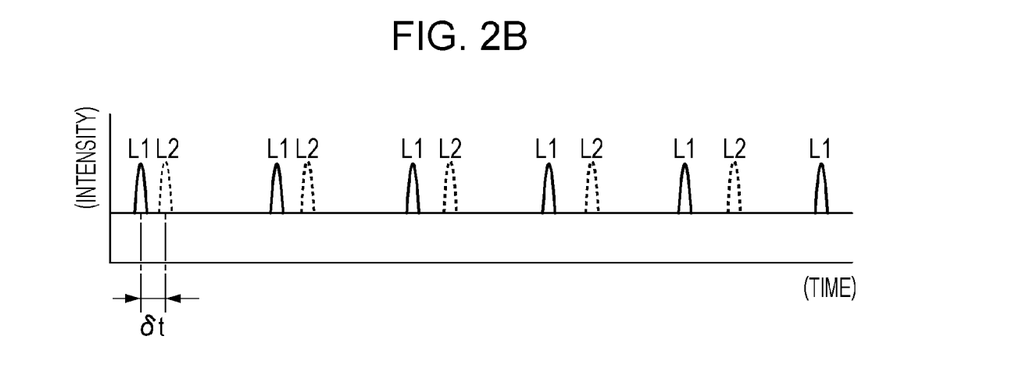
FIG. 2B is a diagram illustrating a difference in arrival time of probe light with reference to pump light.

The laser light source 202 is configured to output an ultra-short laser light pulse. In the photoconductive film 106 of the photoconductive device 101 in the transceiver 201, carriers are generated by excitation caused by illumination of the ultra-short laser light pulse. In this view, in the present description, the ultra-short laser light pulse is called excitation light. As shown in FIG. 2A, the excitation light is split into two optical paths L1 and L2. In the present embodiment, the excitation light passing through L1 is referred to as pump light, and the excitation light passing through L2 is referred to as probe light. After the optical path L2 of the probe light passes through the optical delay unit 203 (described in detail below), the optical path L2 of the probe light is again combined with the optical path L1 of the pump light at (A) immediately before the transceiver 201. The time-domain waveform of the terahertz wave is in the form of a pulse with a width of pico or less seconds, and thus it is difficult to acquire the waveform of the terahertz wave in real time. For this reason, the time-domain waveform of the terahertz wave is acquired via a sampling measurement process using the excitation light. This technique is called a THz-TDS (Terahertz Time Domain Spectroscopy) method. The optical delay unit 203 is configured to adjust sampling points at which data is acquired to produce the time-domain waveform of the terahertz wave. More specifically, as shown in FIG. 2B, the optical delay unit 203 adjusts the delay δt in arrival time, i.e., the difference in arrival time between the pump light (passing through the optical path L1) and the probe light (passing through the optical path L2) that illuminate the transceiver 201.

As described above, the optical delay unit 203 is a unit configured to adjust the arrival time difference δt. The arrival time difference δt may be adjusted by directly adjusting the length of the optical propagation path of the excitation light or by adjusting the effective length of the optical path. A specific method of the direct adjustment of the optical path length is to use a folded optical system in which excitation light is reflected back. The length of the optical path is adjusted by moving this folded optical system in the same direction as the folded direction by using a moving part. A specific method of adjusting the effective length of the optical path is to change a time constant (refractive index) in the optical path along which the excitation light travels. Note that the configuration of the optical delay unit 203 is not limited to that described above, but any other configuration may be employed in the present embodiment as long as the arrival time difference δt can be adjusted.

In the example shown in FIG. 2A, a one-stage folded optical system and a linear motion stage serving as a moving part are used. The length of the optical path L2 from the laser light source 202 to the transceiver 201 is changed by changing the position of the folded optical system by using the moving part. By changing the optical path length, the arrival time difference δt between the pump light and the probe light illuminating the transceiver 201 is adjusted. If the driving speed of the moving part is high, the time-domain waveform of the terahertz wave can be acquired in a short time.

The processing unit 204 provides an external signal to the transceiver 201 via a terminal INPUT whereby the amount of the drawn current is adjusted depending on the amount of the bias applied by the photoconductive device 101 and the output of the photoconductive device 101. The processing unit 204 also serves as a unit that produces a time-domain waveform of the terahertz wave. More specifically, the processing unit 204 produces the time-domain waveform based on the amount of change in the optical path length created by the optical delay unit 203 and the signal provided from the transceiver 201 via the terminal OUTPUT. More specifically, the time-domain waveform is produced by plotting the output of the transceiver 201 in steps of predetermined amount of change in the optical path length. To improve the signal-to-noise ratio of the apparatus, the linear motion stage of the optical delay unit 203 may be stopped at each measurement point (or the speed may be reduced to a level that can be regarded as being substantially at rest), and outputs provided by the transceiver 201 are averaged to obtain a final time-domain waveform. This technique is referred to as a step-and-scan method. An alternative technique is to acquire the time-domain waveform a plurality of times while driving the linear motion stage of the optical delay unit 203 at a high speed. The acquired time-domain waveforms are averaged by the processing unit 204. This technique is referred to as a rapid scan method. Alternatively, priority may be placed on the speed of acquiring the tomographic image (for example, to measure only a particular characteristic part of the waveform) without employing the method described above.

The terahertz wave tomographic image can be acquired from the time-domain waveform of the terahertz wave produced in the above-described manner. In a case where a sample to be measured has an internal refractive-index interface at which the terahertz wave is reflected, the produced time-domain waveform of the terahertz wave includes a plurality of reflected pulses. A one-dimensional tomographic image of the sample along an incident direction of the terahertz wave can be acquired by plotting the time-domain waveform along a distance axis calculated based on the time axis of the time-domain waveform. When the time axis is converted into the distance axis, if the refractive index of the sample located in the propagation path of the terahertz wave is taken into account, it becomes possible to achieve a tomographic image that is closer to a real image. If the sample is moved in a direction normal to a direction in which the terahertz wave is incident, it is possible to acquire a 2-dimensional tomographic image. Furthermore, it is possible to obtain a 3-dimensional tomographic image by moving the sample in a plane with respect to the direction in which the terahertz wave is incident. As described above, the terahertz wave transceiver detects the terahertz-wave pulse passing through the sample irradiated with the terahertz wave generated by the terahertz wave transceiver, and the processing unit produces an image of a structure of the sample in a depth direction based on the positions of the detected terahertz-wave pulses.

As shown in FIG. 2A, the tomographic image acquisition apparatus according to the present embodiment includes the transceiver 201 configured to transmit/receive the terahertz wave. The transceiver 201 is capable of providing substantially equal propagation paths for the terahertz wave traveling toward the sample and the terahertz wave reflected from the sample. This makes it easy for the terahertz wave to be incident on the sample at a normal angle compared with a configuration in which the propagation path for the terahertz wave travelling toward the sample is different from the propagation path for the terahertz wave travelling after being reflected from the sample (i.e., different devices are used to generate and detect the terahertz wave). If the terahertz wave is obliquely incident on the sample, there is a possibility that the terahertz wave is subjected to vignetting depending on the specific incident angle. In the present embodiment, because the terahertz wave is incident on the sample at a right angle, it is easy to minimize the influence of the vignetting on the sample. In the case where the terahertz wave is incident at an oblique angle, an increase occurs in the length of the propagation path of the terahertz wave by an amount corresponding to the incident angle of the terahertz wave, and thus the processing unit 204 needs to correct the tomographic image taking into account the change in the propagation path. In the present embodiment, such a correction is not necessary, which leads to a reduction in load imposed on the operation. Furthermore, it is possible to reduce or minimize the propagation path of the terahertz wave in the inside of the sample compared with the configuration in which the terahertz wave is obliquely incident. This leads to a reduction in influence of scattering or absorption of the terahertz wave that can occur when the terahertz wave travels in the sample. Furthermore, it is possible to reduce the size of the apparatus compared with a system in which generation and detection of a terahertz wave are performed by different separate elements.

Third Embodiment (Location of Transceiver(s) in Tomographic Image Acquisition Apparatus)

Figure 3A:
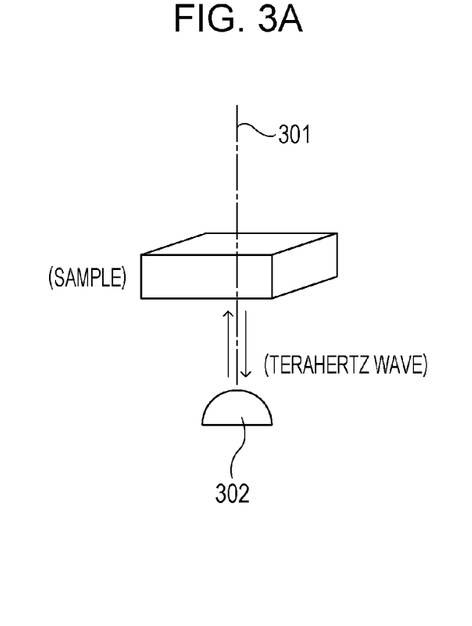
FIGS. 3A to 3C are diagrams illustrating an example of a manner of disposing a transceiver in a tomographic image acquisition apparatus according to an embodiment of the present invention.
Figure 3B:
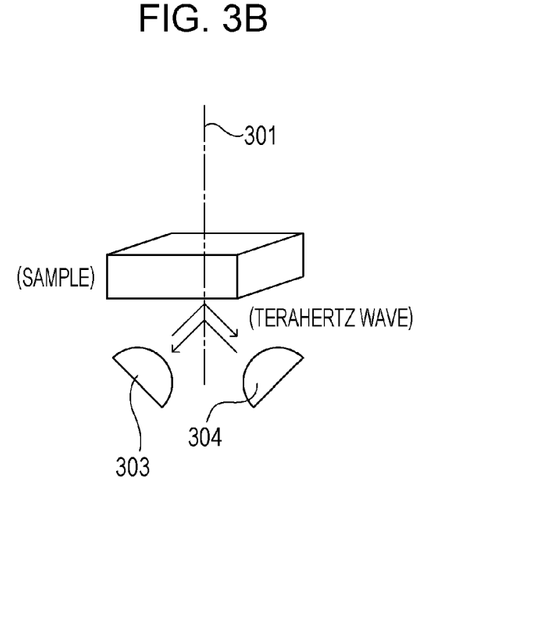
Figure 3C:
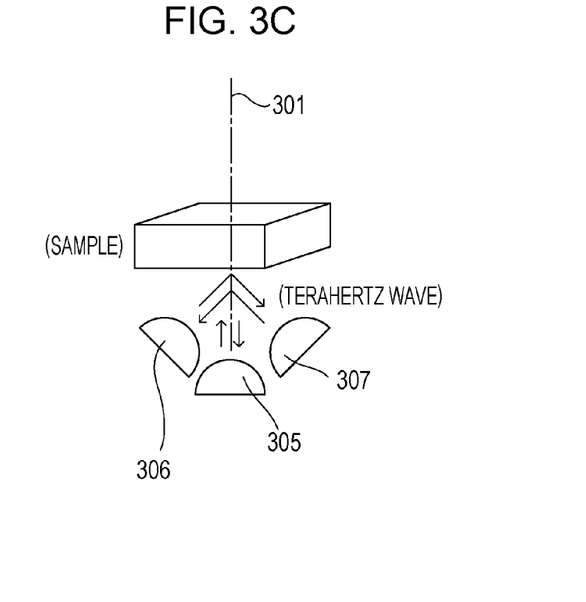

Referring to FIGS. 3A to 3C, a third embodiment is described below. The third embodiment provides examples of modifications of the tomographic image acquisition apparatus according to the second embodiment. More specifically, the third embodiment discloses manners of disposing one or more transceivers in the tomographic image acquisition apparatus. In FIGS. 3A to 3C illustrating examples of manners of disposing terahertz wave transceivers according to the present embodiment, each transceiver configured as shown in FIG. 1 is denoted by one symbol for simplicity of illustration.

FIG. 3A illustrates an example in which a single transceiver 302 is located in an image capturing direction 301, as in the second embodiment described above. Alternatively, a plurality of transceivers may be disposed at different locations around the image capturing direction 301. Note that the image capturing direction 301 does not necessarily refer to a direction of the propagation path along which the terahertz wave travels, but the image capturing direction 301 refers to a general direction in which the terahertz wave is transmitted from an apparatus including the transceiver. The cause the transceiver 302 has the capability of transmitting/receiving terahertz wave, it is possible to reduce the size of the apparatus. In the present embodiment, one or more transceivers each capable of transmitting and receiving a terahertz wave are disposed to acquire signals in a plurality of directions expanding from the image capturing direction 301. More specifically, the plurality of transceivers are disposed at locations that allow the transceivers to transmit and receive the terahertz wave via the sample such that signals in a plurality of directions can be acquired. That is, a plurality of terahertz wave transceivers are disposed around the image capturing direction of the sample such that the terahertz wave transceivers can each transmit a terahertz wave toward the sample and receive the terahertz wave through the sample.

In the example shown in FIG. 3B, a first transceiver 303 and a second transceiver 304 are disposed at locations that are axial symmetry about the image capturing direction 301 of the sample. A terahertz wave transmitted from the first transceiver 303 is received by the second transceiver 304. On the other hand, a terahertz wave transmitted from the second transceiver 304 is received by the first transceiver 303. By disposing the two transceivers in the above-described manner, it becomes possible to acquire signals in two directions in an observation region located in the image capturing direction 301. In this configuration, the pump light and the probe light are commonly used to illuminate both transceivers such that synchronization between the transceivers is achieved. More specifically, for example, light passing through an optical path (to which L1 and L2 are combined together) is split, at a location immediately before the photoconductive device 101 shown in FIG. 2A, into as many beams as there are transceivers used such that the transceivers are illuminated with these split beams. Thus, the arrival time difference δt of excitation light is the same for all transceivers. Therefore, the time-domain waveform of the terahertz wave can be represented along the same time axis for all terahertz waves. Note that it is not necessary to use the same excitation light if synchronization among transceivers can be achieved and the time-domain waveforms of the terahertz waves based on the respective transceivers can be represented along the same time axis. Each transceiver may have associated apparatus elements similar to those shown in FIG. 2A. In this case, it is necessary to achieve synchronization among the associated apparatus elements of the respective transceivers.

In the example shown in FIG. 3C, the configuration shown in FIG. 3A and the configuration shown in FIG. 3B are combined. The terahertz wave transmitted from the first transceiver 305 is received by the same first transceiver 305. The terahertz wave transmitted from the second transceiver 306 is received by a third transceiver 307. The terahertz wave transmitted from the third transceiver 307 is received by the second transceiver 306. In the present embodiment, as described above, terahertz wave transceivers are disposed in different directions (at different angles) with respect to the image capturing direction. Note that the number of transceivers used is not limited to those employed in the above examples.

In the embodiments described above, the transceiver(s) is disposed such that the transceiver(s) receives the terahertz wave reflected from the sample. Alternatively, the transceiver(s) may be disposed such that the transceiver(s) receives the terahertz wave passing through the sample. In any case, it is important to make the configuration such that terahertz waves transmitted from a plurality of transceivers can be mutually received by a proper combination of terahertz waves. In the tomographic image acquisition apparatus, by disposing the transceivers in the above-described manner, it becomes possible to acquire information in different depth directions using the simple configuration. This makes it possible to employ a technique similar to computer tomography, which allows is to easily analyze the structure of the sample.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-175825 filed Aug. 5, 2010, which is hereby incorporated by reference herein in its entirety.

What is claimed is:

1. A terahertz wave transceiver configured to generate and detect terahertz waves based on time-domain spectroscopy, comprising:

a photoconductive device including a photoconductive film, a first electrode, and a second electrode configured such that the first and second electrodes are disposed on the photoconductive film and such that the first and second electrodes oppose each other via an excitation light illumination region;

a bias applying unit connected to the first electrode and configured to apply a bias between the first electrode and the second electrode to generate a terahertz wave in the excitation light illumination region;

a current detection unit connected to the second electrode and configured to detect a terahertz-wave current that is a component of a current generated in the excitation light illumination region and that is generated by an electric field of a received terahertz wave; and a current drawing unit connected to the second electrode and configured to draw a current originating from the bias applied by the bias applying unit, wherein the current drawing unit includes an adjustment unit configured to determine the amount of the current drawn, based on the amount of the bias applied by the bias applying unit.

2. The terahertz wave transceiver according to claim 1, wherein the bias applied by the bias applying unit includes an AC component.

3. A tomographic image acquisition apparatus comprising:
a terahertz wave transceiver according to claim 1; and
a processing unit, wherein
the terahertz wave transceiver detects the received terahertz-wave which is radiated from a sample irradiated with the terahertz wave generated by the terahertz wave transceiver, and
the processing unit produces an image of a structure of the sample in a depth direction based on a position of the detected terahertz-wave pulse.

4. The tomographic image acquisition apparatus according to claim 3, comprising a plurality of terahertz wave transceivers located in a direction of capturing an image of the sample, wherein
the terahertz wave transceivers are disposed at locations that allow the terahertz wave transceivers to transmit a terahertz wave toward the sample and receive a resulting terahertz wave through the sample.

5. The terahertz wave transceiver according to claim 1, wherein the current drawing unit draws the current generated in the photoconductive device due to the bias so as to prevent or reduce flowing of the bias current into the current detection unit.

6. A tomographic image acquisition apparatus comprising:
a plurality of terahertz wave transceivers according to claim 1; and
a processing unit, wherein
the plurality of terahertz wave transceivers detect the received terahertz-wave which is radiated from a sample irradiated with the terahertz waves generated by the plurality of terahertz wave transceivers, and
the processing unit produces an image of a structure of the sample in a depth direction based on a position of the detected terahertz-wave.

7. The tomographic image acquisition apparatus according to claim 6, wherein the plurality of terahertz wave transceivers are located in a direction of capturing an image of the sample.

* * * * *